United States Patent [19]

Kan et al.

[11] Patent Number: 4,524,070
[45] Date of Patent: Jun. 18, 1985

[54] AMINATED DERIVATIVES OF PYRIDAZINE SUBSTITUTED IN 6 POSITION BY A HETEROCYCLE OR AN ALICYCLE AND COMPOSITIONS, SAID DERIVATIVES BEING ACTIVE ON THE CENTRAL NERVOUS SYSTEM

[75] Inventors: Jean-Paul Kan; Kathleen Biziere, both of Clapiers; Camille-Georges Wermuth, Strasbourg, all of France

[73] Assignee: Sanofi, Paris, France

[21] Appl. No.: 571,698

[22] Filed: Jan. 18, 1984

[30] Foreign Application Priority Data

Jan. 24, 1983 [FR] France ................ 83 01029

[51] Int. Cl.$^3$ ................ A61K 31/535; C07D 413/12
[52] U.S. Cl. ................ 514/230; 514/237; 544/114
[58] Field of Search ................ 544/114; 424/248.51, 424/248.56

[56] References Cited

U.S. PATENT DOCUMENTS 3,825,540  7/1974  Laborit ................ 544/114

FOREIGN PATENT DOCUMENTS 1345880  2/1974  United Kingdom .

OTHER PUBLICATIONS

Chemical Abstracts, vol. 76, No. 7, Feb. 14, 1972, p. 22, No. 41974h, Columbus, Ohio, (USA); M. R. Ornellas: "Biochemical Studies of Cerebral Subfractions After Chronic Administration of 4-methyl-3-[2-(morpholino)ethylamino]-6-phenylpyridazine hydrochloride, AG 620", & Biochem. Pharmacol., 1971, 20(9), 2141-7.

Chemical Abstracts, vol. 73, No. 1, Jul. 6, 1970, p. 199, No. 12845z, Columbus, Ohio, (USA); M. R. Ornellas et al.: "Pharmacological Interpretation of the Energy Metabolism of Rat Brain in vivo and in vitro in Connection With a Study on Some Pyridazines", & Agressologie, 1969, 10(6), 437-49.

Primary Examiner—Robert W. Ramsuer
Attorney, Agent, or Firm—Bacon & Thomas

[57] ABSTRACT

The present invention relates to aminated derivatives of pyridazine of formula:

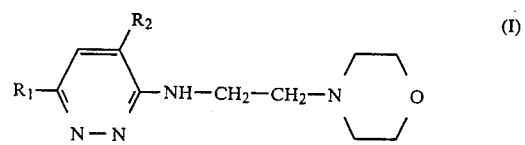

in which:
- $R_1$ designates a 2-thienyl, 3-thienyl or cyclohexyl group;
- $R_2$ represents a lower alkyl group (1 to 4 atoms of carbon), or an atom of hydrogen as well as the salts of said derivatives with the acids; which compounds effect the central nervous system and may be used in human medicine to treat depression. It also relates to a process for preparing said derivatives and the drugs containing them.

6 Claims, No Drawings

AMINATED DERIVATIVES OF PYRIDAZINE SUBSTITUTED IN 6 POSITION BY A HETEROCYCLE OR AN ALICYCLE AND COMPOSITIONS, SAID DERIVATIVES BEING ACTIVE ON THE CENTRAL NERVOUS SYSTEM

The present invention relates to derivatives of pyridazine; it also relates to a process for preparing said derivatives and to the drugs which contain at least one of said derivatives as active ingredient.

The compounds according to the invention correspond to general formula:

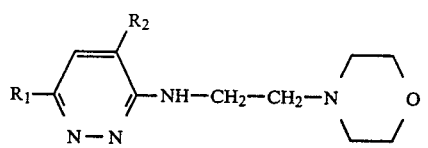

in which:

$R_1$ designates a 2-thienyl, 3-thienyl or cyclohexyl group;

$R_2$ represents a lower alkyl group (1 to 4 atoms of carbon), or an atom of hydrogen.

The present invention also relates to addition salts which are yielded by compounds (I) with the pharmaceutically acceptable inorganic or organic acids.

It also includes a process for preparing the compounds of formula (I) as well as the application thereof in therapeutics.

The compounds according to the invention are obtained from a suitably substituted 3-chloro pyridazine 1 by action of the amine

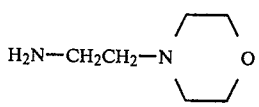

in accordance with the reaction scheme:

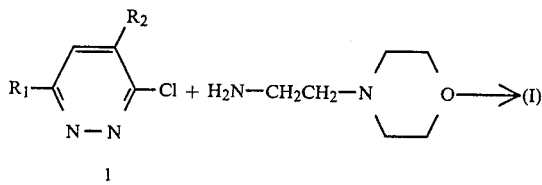

The reaction between the chlorinated derivative 1 and the amine 2 is effected by heating within a suitable solvent, such as an alcohol, most often at boiling temperature of the solvent. Reaction is carried out in the presence of a hydracid acceptor intended to fix the hydrochloric acid formed; an excess of the amine 2 is most often used as such.

Product (I) is isolated by dilution of the reaction mixture with water and extraction by a suitable solvent, such as ethyl acetate or ether.

Compounds (I) may be salified in conventional manner by action of the acid on a hot solution of the base, the solvent being selected so that the salt crystallizes by cooling or by addition of another solvent.

The chlorinated derivatives 1 may be prepared in accordance with the known methods, particularly according to the following reaction diagram:

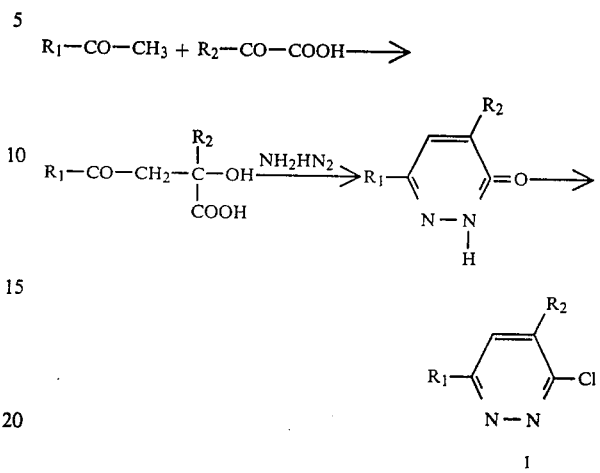

which consists in condensing the ketone $R_1$—CO—CH$_3$ with the α-ketoacid $R_2$—CO—COOH to obtain the corresponding α-hydroxygammaketonic acid. By action of hydrazine, the latter leads to the corresponding 3-pyridazone which, in turn, by action of phosphorus oxychloride, yields the 3-chloro pyridazine 1.

The following non-limiting Examples are given by way of illustration of the present invention.

EXAMPLE 1

3-morpholinoethylamino-4-methyl-6-(2-thienyl)pyridazine, dihydrochloride; (CM 30387)

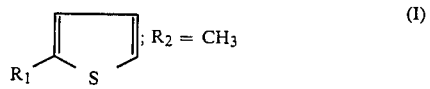

(a) 2-hydroxy-2-methyl-3-(2-thenoyl)propanoic acid 70.4 g of pyruvic acid are neutralized by a 20% potassium hydroxide solution with stirring and cooling, then 101 g of 2-acetyl thiophene are added. A solution of 56 g of potassium hydroxide in 1600 ml of methanol is then added with stirring then the mixture is left in the refrigerator for 4 days.

The solution is acidified by 10N sulfuric acid up to pH 3–4. The precipitate of potassium sulfate is filtered and the methanol is evaporated by water-bath in vacuo. The remaining solution is acidified by 10N sulfuric acid and water is added to dissolve the potassium sulfate. The mixture is extracted with ether and the ethereal phase is washed twice with 100 ml of water. The organic solution is extracted with an aqueous 10% potassium bicarbonate solution. The aqueous phase is separated and extracted with a little ether, then acidified by addition of 10N sulfuric acid.

The expected acid crystallizes; it is drained and washed with a little isopropyl ether. It is used as such for the following step.

(b) 4-methyl-6-(2-thienyl)-3-pyridazone 20 g of the acid obtained above are dissolved in 200 ml of butanol then 7 g of hydrazine hydrate are added.

The mixture is taken to reflux, slowly distilling the butanol-water azeotrope formed. When the formation of water has ceased, about 160 ml of butanol are distilled and left to crystallize by cooling.

The crystals are drained and recrystallization takes place in acetic acid. Weight: 14.5 g; melting point: 236° C.

(c) 3-chloro-4-methyl-6-(2-thienyl)pyridazine

The mixture of 14 g of pyridazone obtained above and 90 ml of phosphorus oxychloride is heated by water-bath for 3 hours. The mixture is poured over crushed ice and is rendered alkaline by a 20% sodium hydroxide solution.

The solid is drained and recrystallization takes place in methanol. Weight: 10.5 g; melting point: 146° C.

(d) CM 30387

The mixture of 10.11 g of chloropyridazine obtained above and 18.9 g of 2-morpholino ethylamine in 150 ml of butanol is heated to reflux for 3 days.

The solution is poured into water and rendered alkaline with a sodium hydroxide solution. The mixture is extracted with ether, dried over sodium sulfate and concentrated to dryness in vacuo.

The residue crystallizes and is recrystallized in ethyl acetate. Weight: 9 g; melting point: 132° C.

Dihydrochloride

To the solution of 8.9 g of the above base in 50 ml of isopropanol are added 5.5 ml of an aqueous solution of concentrated hydrochloric acid. The solid formed is drained and recrystallized in absolute ethanol. Weight: 10.6 g; melting point: 234° C.

EXAMPLE 2

3-morpholinoethylamino-4-methyl-6-(3-thienyl)-pyridazine, dihydrochloride; (CM 30388)

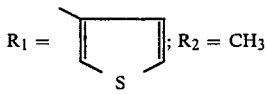

$R_1 =$ [thienyl]; $R_2 = CH_3$   (I)

By operating as in Example 1, but by replacing the 2-acetyl thiophene by 3-acetyl thiophene, the following are successively obtained:

2-hydroxy-2-methyl-6-(3-thenoyl)propanoic acid;
4-methyl-6-(3-thienyl)-3-pyridazine; m.p.: 246° C. (acetic acid)
3-chloro-4-methyl-6-(3-thienyl)pyridazine; m.p.: 171° C. (dioxane);
CM 30388
Base: m.p.: 56° C. (ethyl acetate—petroleum ether)
Dihydrochloride: melting point: 152° C. (absolute alcohol).

EXAMPLE 3

3-morpholinoethylamino-4-methyl-6-cyclohexyl-pyridazine; dihydrochloride; CM 30390

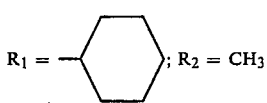

$R_1 =$ [cyclohexyl]; $R_2 = CH_3$   (I)

By operating as in Example 1, but by replacing the 2-acetyl thiophene by cyclohexylmethylketone, the following are successively obtained:

2-hydroxy-2-methyl 6-cyclohexyl-propanoic acid;
4-methyl-6-cyclohexyl-3-pyridazone; m.p.: 173° C. (isopropanol-isopropyl ether);
3-chloro-4-methyl-6-cyclohexyl-pyridazine chromatographed over silica, eluting with ethyl acetate-hexane (25–75 vol/vol);
CM 30390
Base: yellow oil
Dihydrochloride: m.p. 237° C. (isopropanol-ether).

The products of the invention were subjected to pharmacological tests with a view to determining their activity on the central nervous system. The various trials to which the products were subjected will be indicated hereinafter.

I

ANTIDEPRESSIVE ACTIVITY

Antagonism of ptosis induced by reserpine

This test described by GOURET (Journal de Pharmacologie, Paris, 1973, 4 (1), 105–128) was carried out on the female CDI (Charles River) mouse weighing 20±1 g. Reserpine induces a ptosis 1 hour after its intravenous administration; certain antidepressants oppose this ptosis.

The following protocol was chosen.

The substances to be studied were administered i.p. The reserpine was administered simultaneously by the intravenous route at the dose of 2 mg/kg. 1 hour after administration of reserpine, the number of animals not presenting ptosis was noted.

This test was carried out on batches of 10 mice and the percentage of animals not presenting ptosis was determined. The results are expressed in effective dose 50 ($ED_{50}$) or dose preventing ptosis in 50% of the animals treated.

Potentialization of the head twitches induced by 5-hydroxytryptophane

The 5-hydroxytryptophane, precursor of the 5-hydroxytryptamine, induces in the mouse typical behaviour characterized by sudden head twitches. The molecules which activate the central serotoninergic transmission increase the number of head twitches, whilst the tricyclic antidepressants are inactive.

At time zero, the product to be studied is administered by the intraperitoneal route then, 1 hour afterwards, a single dose (200 mg/kg) of l-5-hydroxytryptophane in suspension in distilled water is in turn administered by the same route. Each animal (female CDI Charles River mouse weighing from 22 to 24 g) is immediately placed in a cylindrical glass beaker. The number of head twitches is counted for 20 minutes.

For each dose of the product to be tested, batches of 10 animals are experimented on, in comparison with a control batch which receives only the vehicle.

The results are expressed in % with respect to the average score obtained in the control mice.

Measurement of the MAO A activity in vitro

The inhibitory activity of the monoamine oxydase A is assessed in accordance with the method described by KAN et al (Life Sciences 26, 2165–2171, 1980), using the striatum of rate as source of enzyme.

After dissection, the tissues are homogenized in 16 volumes (weight per volume) of iced phosphate buffer (0.1M, pH=7.40). Fractions of 0.1 ml are incubated for 10 minutes in the presence of 5-hydroxytryptamine labelled with carbon-14 (final concentration 480 μM)

and of variable concentrations of the product to be tested; the final volume of incubation is 0.5 ml. The acid metabolites are extracted in 7 ml of a toluene/ethyl acetate (1:1, vol/vol) mixture then counted by liquid scintillation. The concentration of the product tested which inhibits the control activity by 50% ($I.C._{50}$) is determined graphically.

II

DOPAMINERGIC ACTIVITY

This was studied by analysis of the behaviour of rotation in the mouse after unilateral lesion of the striatum (P. Protais et al., J. Pharmacol., 1976, 7, 251).

Female Charles River CDI mice weighing from 20 to 24 g were previously subjected to a unilateral lesion of the striatum by stereotaxic injection of 6-hydroxydopamine at the rate of 8 mcg per animal. One week after this operation, the products to be studied were administered by the intraperitoneal route to groups of 7 mice. 1 hour after administration of the product, the number of rotations is determined for a period of 2 minutes. The rotations ispilateral with respect to the lesion are counted positively and the contralateral rotations are counted negatively.

The algebraic sum of the rotations for a group of treated animals is compared with that of the group of control animals having received only the vehicle (physiological serum).

The results are expressed in % variation of the rotations of the treated animals with respect to the control animals.

III

CHOLINERGIC ACTIVITY

The cholinergic receptors of muscarinic type may be labelled in vitro by tritiated quinuclidinyl-benzylate (QNB [$^3H$]). Such labelling is effected in accordance with the technique described by YAMAMURA et coll. (Proceedings of the National Academy of Sciences of the USA, 71, 1725-9 (1974).

Rats' cerebra from which the cerebellum has been removed are homogenized in 10 volumes (weight per volume) of 0.32M sucrose, then centrifuged at $1000 \times g$ of 10 minutes. The concentrate is eliminated and the supernatant matter is rehomogenized.

Aliquot fractions of 0.1 ml are incubated at 25° C. for 1 hour in 2 ml of phosphate buffer (0.05M, pH=7.4) containing variable concentrations of product to be tested and 0.05 nM of QNB ($^3H$).

The samples are then filtered on Whatman GF/B filters under reduced pressure then washed by the incubation buffer. The radioactivity absorbed on the filters is counted by liquid scintillation.

Non-specific fixation is determined in the presence of 100 μM of oxotremorine. The $IC_{50}$s are determined graphically.

The results obtained with the products of the invention are shown in the Table hereinbelow.

This Table also shows the results obtained for the same tests with a product of the prior art belonging to the chemical family of pyridazines, designated under the name Minaprine (DCI) and responding to formula:

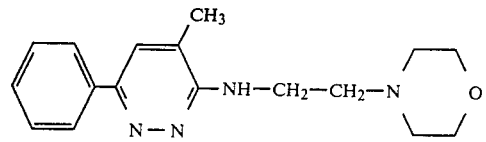

The results obtained with the products of the invention show that:

as antidepressant, they present a better serotoninomimetic activity (5-HTP test) and a better monoamine oxydase inhibitory activity than the reference product;

they are more active as cholinomimetic agents (bond with $^3H$-QNB) than the reference product;

contrary to the reference product, they are bereft of any dopaminomimetic activity.

Furthermore, the products according to the invention are of low toxicity and may therefore be used in human medicine for the treatment of depressions and depressive states of any nature.

These products may be administered by the oral, rectal or injectable route. The pharmaceutical compositions containing them may be solid or liquid, in the form of tablets, capsules, granules, suppositories or injectable preparations.

Posology may vary in large proportions depending on the mode of administration and on the type and seriousness of the disorder to be treated.

In the adult, by the oral route, it is most often between 0.010 and 0.500 g, possibly spread out in several doses.

By way of example, the following Galenic preparation may be indicated:

| CAPSULES | |
|---|---|
| CM 30388 | 100 mg |
| Aerosil | 0.5 mg |
| Magnesium stearate | 1.5 mg |
| STA RX 1500 starch | 48 mg |
| | 150 mg |

TABLE

| Product No. | Ptosis induced by reserpine $ED_{50}$ mg/kg | 5-HTP test % variation (dose in mg/kg) | MAO A Inhibition ($IC_{50}$, mg/kg) | Bond with QNB ($^3H$) ($IC_{50}$, M) | Rotations test % variation (dose in mg/kg) |
|---|---|---|---|---|---|
| CM 30387 | 4.8 | 632**(8) | 10 | $2.4 \times 10^{-5}$ | Inactive at 10 |
| CM 30388 | 10.3 | 647**(8) | 7.8 | $1.8 \times 10^{-5}$ | Inactive at 10 |
| CM 30390 | 4.5 | 219*(7.5) | — | $1.4 \times 10^{-5}$ | Inactive at 10 |
| Minaprine | 5 | 257*(10) | 16 | $10^{-4}$ | −79**(0.5) |

*p 0.05
**p 0.01

What is claimed is:

1. Aminated derivatives of pyridazine of formula:

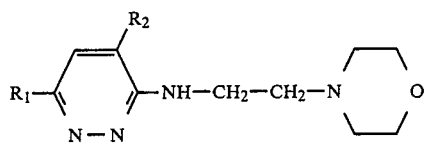 (I)

in which $R_1$ represents a 2-thienyl, 3-thienyl or cyclohexyl group; $R_2$ represents a lower alkyl group having 1 to 4 carbon atoms, or a hydrogen atom, and acid addition salts thereof.

2. The compound of claim 1 which is 3-morpholinoethylamino-4-methyl-6-(2-thienyl)pyridazine or an acid addition salt thereof.

3. The compound of claim 1 which is 3-morpholinoethylamino-4-methyl-6-(3-thienyl)-pyridazine or an acid addition salt thereof.

4. The compound of claim 1 which is 3-morpholinoethylamino-4-methyl-6-cyclohexyl-pyridazine or an acid addition salt thereof.

5. A pharmaceutical composition active on the central nervous system comprising a compound of claim 1 and a pharmaceutically acceptable carrier.

6. The composition of claim 5 adopted for oral administration and containing from 0.01 to 0.50 g of the compound of claim 1.

* * * * *